United States Patent [19]

Truckai et al.

[11] Patent Number: 5,769,880
[45] Date of Patent: Jun. 23, 1998

[54] MOISTURE TRANSPORT SYSTEM FOR CONTACT ELECTROCOAGULATION

[75] Inventors: Csaba Truckai, Sunnyvale, Calif.; David C. Auth, Kirkland, Wash.

[73] Assignee: Novacept, Palo Alto, Calif.

[21] Appl. No.: 632,516

[22] Filed: Apr. 12, 1996

[51] Int. Cl.$^6$ ............................................. A61F 2/00
[52] U.S. Cl. ........................... 607/101; 607/99; 607/116; 604/20; 604/49; 604/55; 604/114
[58] Field of Search .................................... 604/113, 114, 604/20, 21, 49, 55; 607/1, 101, 98, 99, 115, 116

[56] References Cited

U.S. PATENT DOCUMENTS

| | | |
|---|---|---|
| 1,620,929 | 3/1927 | Wallerich . |
| 1,827,306 | 10/1931 | Chapman et al. . |
| 2,190,383 | 2/1940 | Newman ................................. 128/401 |
| 2,466,042 | 4/1949 | Reich et al. ............................. 128/401 |
| 3,645,265 | 2/1972 | Majzlin ............................... 128/303.13 |
| 3,840,016 | 10/1974 | Lindemann ......................... 128/303.17 |
| 3,924,628 | 12/1975 | Droegemueller et al. ........... 128/303.1 |
| 3,948,270 | 4/1976 | Hasson ................................... 128/348 |
| 4,057,063 | 11/1977 | Gieles et al. ....................... 128/303.17 |
| 4,449,528 | 5/1984 | Auth et al. ............................... 606/31 |
| 4,492,231 | 1/1985 | Auth ......................................... 606/42 |
| 4,532,924 | 8/1985 | Auth et al. ............................... 606/50 |
| 4,582,057 | 4/1986 | Auth et al. ............................... 606/31 |
| 4,601,698 | 7/1986 | Moulding, Jr. ........................... 604/55 |
| 4,662,383 | 5/1987 | Sogawa et al. ........................ 128/784 |
| 4,676,258 | 6/1987 | Inokuchi et al. ...................... 128/804 |
| 4,691,703 | 9/1987 | Auth et al. ............................... 606/31 |
| 4,832,048 | 5/1989 | Cohen ................................... 128/786 |
| 4,865,047 | 9/1989 | Chou et al. ............................ 128/784 |
| 4,949,718 | 8/1990 | Neuwirth et al. ...................... 128/401 |
| 4,960,133 | 10/1990 | Hewson ................................. 128/784 |
| 4,961,435 | 10/1990 | Kitagawa et al. ..................... 128/788 |
| 4,979,948 | 12/1990 | Geddes et al. ........................... 606/33 |
| 5,057,106 | 10/1991 | Kasevich et al. ........................ 606/33 |
| 5,084,044 | 1/1992 | Quint ........................................ 606/27 |
| 5,105,808 | 4/1992 | Neuwirth et al. ...................... 128/784 |
| 5,147,353 | 9/1992 | Everett .................................... 606/15 |
| 5,159,925 | 11/1992 | Neuwirth et al. ...................... 128/401 |
| 5,186,181 | 2/1993 | Franconi et al. ....................... 128/804 |
| 5,188,122 | 2/1993 | Phipps et al. .......................... 128/788 |
| 5,188,602 | 2/1993 | Nichols .................................... 604/96 |
| 5,227,201 | 7/1993 | Stern ........................................ 607/98 |
| 5,248,312 | 9/1993 | Langberg ................................. 606/28 |
| 5,308,327 | 5/1994 | Heaven et al. .......................... 604/96 |
| 5,334,193 | 8/1994 | Nardella ................................... 606/41 |
| 5,364,393 | 11/1994 | Auth ......................................... 606/34 |
| 5,433,708 | 7/1995 | Nichols et al. ........................ 604/113 |
| 5,437,629 | 8/1995 | Goldrath ................................. 604/21 |
| 5,443,470 | 8/1995 | Stern et al. .............................. 607/98 |
| 5,505,730 | 4/1996 | Edwards ................................... 606/41 |

FOREIGN PATENT DOCUMENTS

| | | |
|---|---|---|
| 0584930A1 | 3/1994 | European Pat. Off. . |
| WO 92/19145 | 11/1992 | WIPO . |
| WO 94/07445 | 4/1994 | WIPO . |
| WO 94/10948 | 5/1994 | WIPO . |
| WO 94/23794 | 10/1994 | WIPO . |
| WO 95/04385 | 2/1995 | WIPO . |
| WO 95/07664 | 2/1995 | WIPO . |
| WO 95/05869 | 3/1995 | WIPO . |
| WO 95/10326 | 4/1995 | WIPO . |

*Primary Examiner*—Michael Buiz
*Assistant Examiner*—N. Kent Gring
*Attorney, Agent, or Firm*—Limbach & Limbach L.L.P.

[57] ABSTRACT

An apparatus and method for use in performing ablation of organs and other tissue includes an electrode carrying member which is substantially absorbent and/or permeable to moisture. The electrode carrying member is mounted to the distal end of an elongate shaft, and an array of electrodes is mounted to the surface of the electrode carrying member. Following placement of the ablation device into contact with the tissue to be ablated, an RF generator is used to deliver RF energy to the electrodes and to thereby induce current flow from the electrodes to tissue to be ablated. As the current heats the tissue, moisture (such as water vapor or liquid) leaves the tissue causing the tissue to dehydrate. The moisture permeability and/or absorbency of the electrode carrying member allows the moisture to leave the ablation site so as to prevent the moisture from providing a path of conductivity for the current.

33 Claims, 7 Drawing Sheets

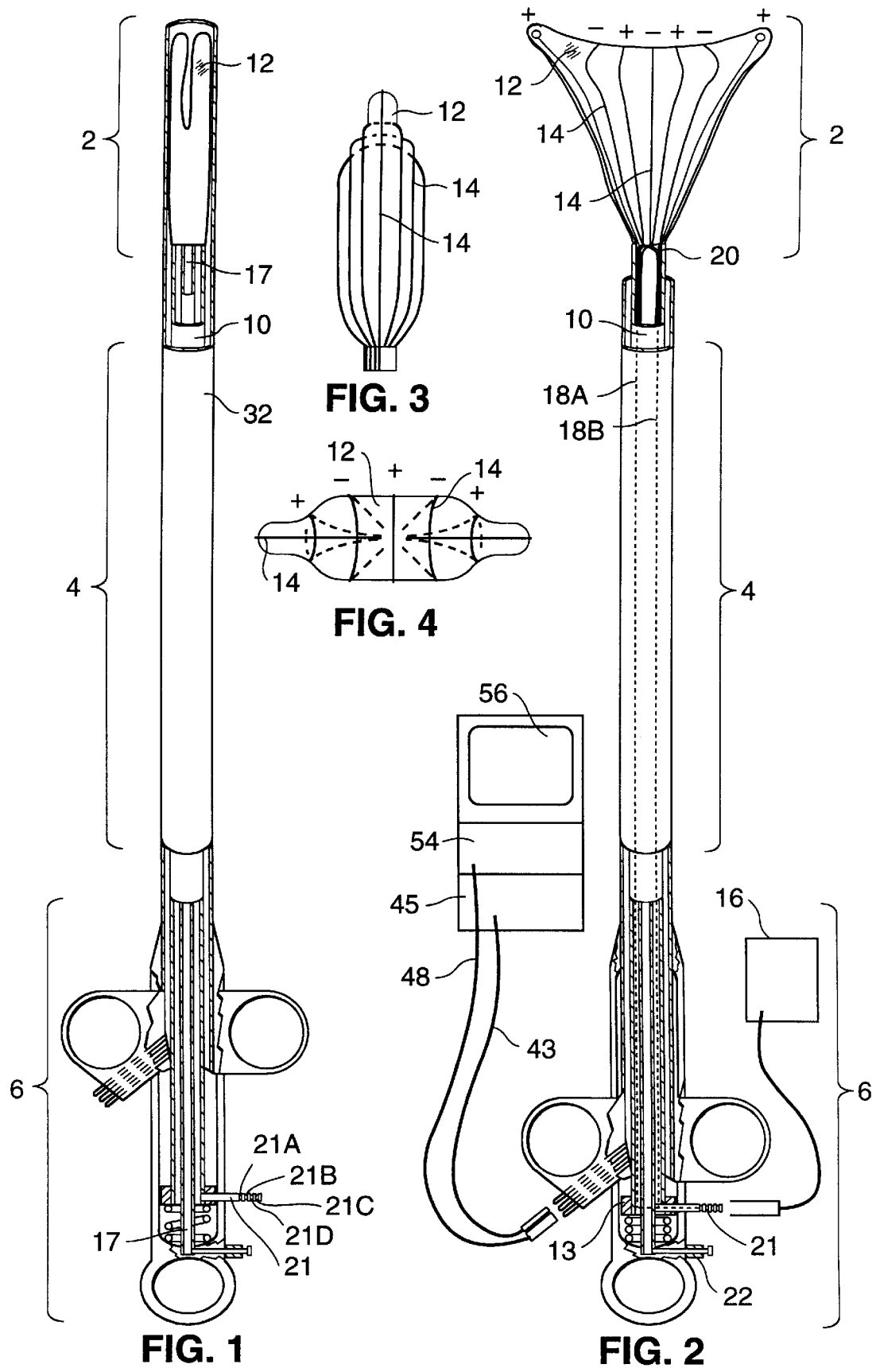

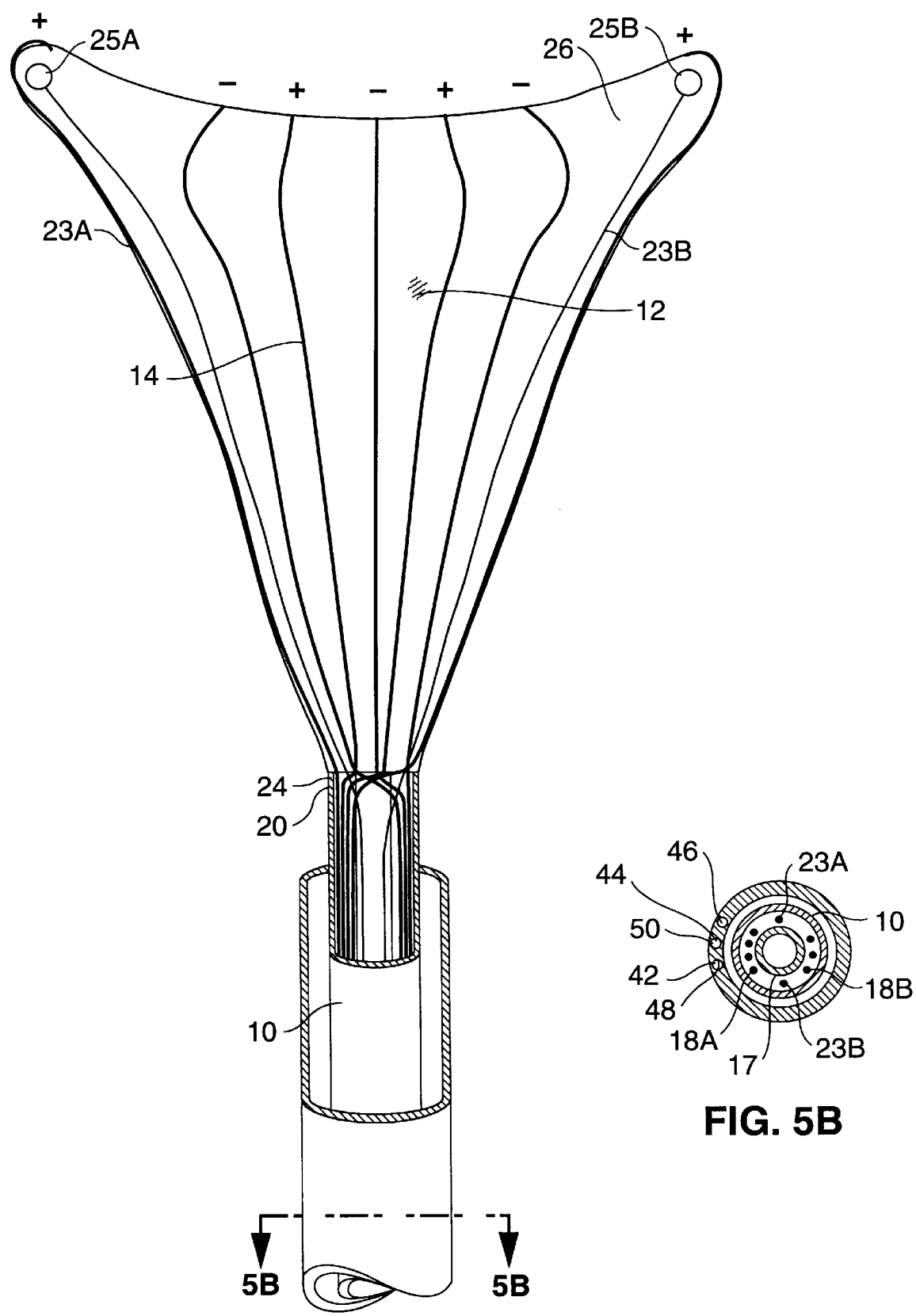

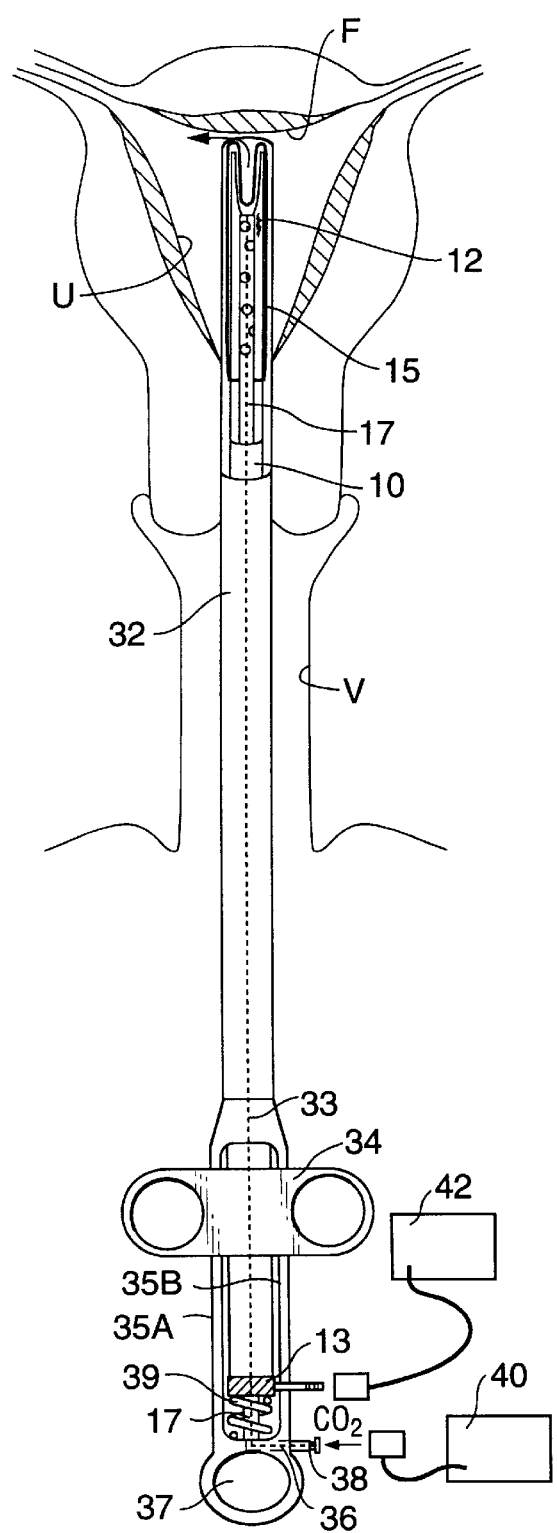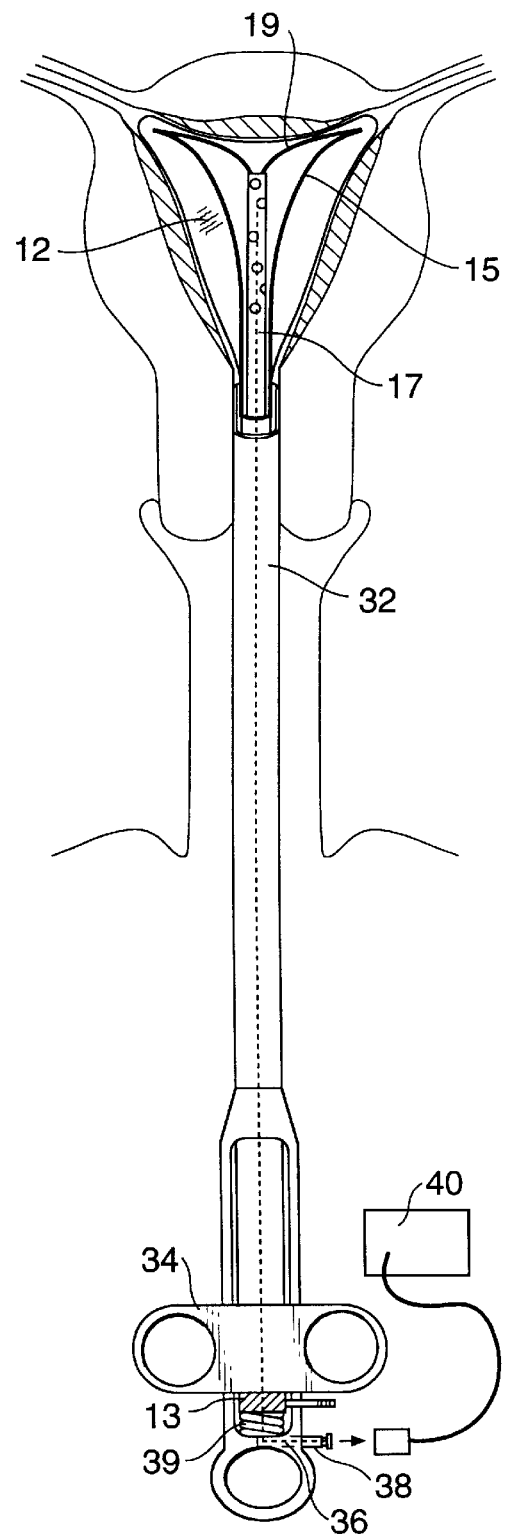

5,769,880

MOISTURE TRANSPORT SYSTEM FOR CONTACT ELECTROCOAGULATION

FIELD OF THE INVENTION

The present invention relates generally to the field of apparatuses and methods for ablating or coagulating the interior surfaces of body organs. Specifically, it relates to an apparatus and method for ablating the interior linings of body organs such as the uterus and gallbladder.

BACKGROUND OF THE INVENTION

Ablation of the interior lining of a body organ is a procedure which involves heating the organ lining to temperatures which destroy the cells of the lining or coagulate tissue proteins for hemostasis. Such a procedure may be performed as a treatment to one of many conditions, such as chronic bleeding of the endometrial layer of the uterus or abnormalities of the mucosal layer of the gallbladder. Existing methods for effecting ablation include circulation of heated fluid inside the organ (either directly or inside a balloon), laser treatment of the organ lining, and resistive heating using application of RF energy to the tissue to be ablated.

U.S. Pat. No. 5,084,044 describes an apparatus for endometrial ablation in which a bladder is inserted into the uterus. Heated fluid is then circulated through the balloon to expand the balloon into contact with the endometrium and to ablate the endometrium thermally. U.S. Pat. No. 5,443,470 describes an apparatus for endometrial ablation in which an expandable bladder is provided with electrodes on its outer surface. After the apparatus is positioned inside the uterus, a non-conductive gas or liquid is used to fill the balloon, causing the balloon to push the electrodes into contact with the endometrial surface. RF energy is supplied to the electrodes to ablate the endometrial tissue using resistive heating.

These ablation devices are satisfactory for carrying out ablation procedures. However, because no data or feedback is available to guide the physician as do how deep the tissue ablation has progressed, controlling the ablation depth and ablation profile with such devices can only be done by assumption.

For example, heated fluid method is a very passive and ineffective heating process which relies on the heat conductivity of the tissue. This process does not account for variations in factors such as the amount of contact between the balloon and the underlying tissue, or cooling effects such as those of blood circulating through the organ. RF ablation techniques can achieve more effective ablation since it relies on active heating of the tissue using RF energy, but presently the depth of ablation using RF techniques can only be estimated by physician since no feedback can be provided as to actual ablation depth.

Both the heated fluid techniques and the latest RF techniques must be performed using great care to prevent overablation. Monitoring of tissue surface temperature is normally carried out during these ablation procedures to ensure the temperature does not exceed 100° C. If the temperature exceeds 100° C., the fluid within the tissue begins to boil and to thereby produce steam. Because ablation is carried out within a closed cavity within the body, the steam cannot escape and may instead force itself deeply into the tissue, or it may pass into areas adjacent to the area intended to be ablated, causing embolism or unintended burning.

Moreover, in prior art RF devices the water drawn from the tissue creates a path of conductivity through which current traveling through the electrodes will flow. This can prevent the current from traveling into the tissue to be ablated. Moreover, the presence of this current path around the electrodes causes current to be continuously drawn from the electrodes. The current heats the liquid drawn from the tissue and thus turns the ablation process into a passive heating method in which the heated liquid around the electrodes causes thermal ablation to continue well beyond the desired ablation depths.

Another problem with prior art ablation devices is that it is difficult for a physician to find out when ablation has been carried out to a desired depth within the tissue. Thus, it is often the case that too much or too little tissue may be ablated during an ablation procedure.

It is therefore desirable to provide an ablation device which eliminates the above-described problem of steam and liquid buildup at the ablation site. It is further desirable to provide an ablation method and device which allows the depth of ablation to be controlled and which automatically discontinues ablation once the desired ablation depth has been reached.

SUMMARY OF THE INVENTION

An apparatus and method for use in performing ablation or coagulation of organs and other tissue includes an electrode carrying member which is substantially absorbent and/or permeable to moisture and gases such as steam and conformable to the body cavity. Suctioning means may additionally be positioned within the electrode carrying member to aide the removal of moisture, and/or gas and/or liquid, present or generated during the ablation procedure. An array of electrodes is mounted to the surface of the electrode carrying member and arranged to produce ablation to a predetermined depth. The electrodes may be provided with means for variably controlling ablation depth by changing the electrode density or center to center spacing.

Following placement of the ablation device into contact with the tissue to be ablated, an RF generator is used to deliver RF energy to the electrodes and to thereby induce current flow from the electrodes to tissue to be ablated. As the current heats the tissue, moisture (such as steam or liquid) leaves the tissue causing the tissue to dehydrate. The moisture permeability and/or absorbency of the electrode carrying member allows the moisture to leave the ablation site so as to prevent the moisture from providing a path of conductivity for the current.

BRIEF DESCRIPTION OF THE DRAWINGS

FIG. 1 is a front elevation view of an ablation device according to the present invention, with the handle shown in cross-section and with the RF applicator head in a closed condition.

FIG. 2 is a front elevation view of an ablation device according to the present invention, with the handle shown in cross-section and with the RF applicator head in an open condition.

FIG. 3 is a side elevation view of the ablation device of FIG. 2.

FIG. 4 is a top plan view of the ablation device of FIG. 2.

FIG. 5A is a front elevation view of the applicator head and a portion of the main body of the ablation device of FIG. 2, with the main body shown in cross-section.

FIG. 5B is a cross-section view of the main body taken along the plane designated 5B—5B in FIG. 5A.

FIG. 6 is a schematic representation of a uterus showing the ablation device of FIG. 1 following insertion of the device into the uterus but prior to retraction of the introducer sheath and activation of the spring members.

FIG. 7 is a schematic representation of a uterus showing the ablation device of FIG. 1 following insertion of the device into the uterus and following the retraction of the introducer sheath and the expansion of the RF applicator head.

DETAILED DESCRIPTION

Figure 8:
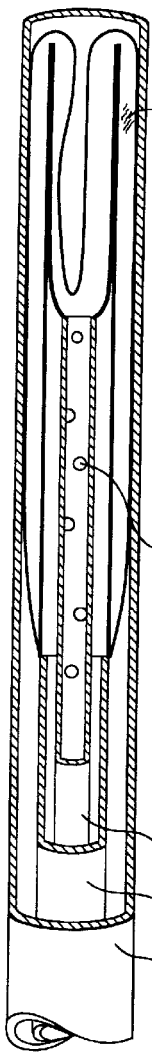
FIG. 8 is a cross-section view of the RF applicator head and the distal portion of the main body of the apparatus of FIG. 1, showing the RF applicator head in the closed condition.
Figure 9:
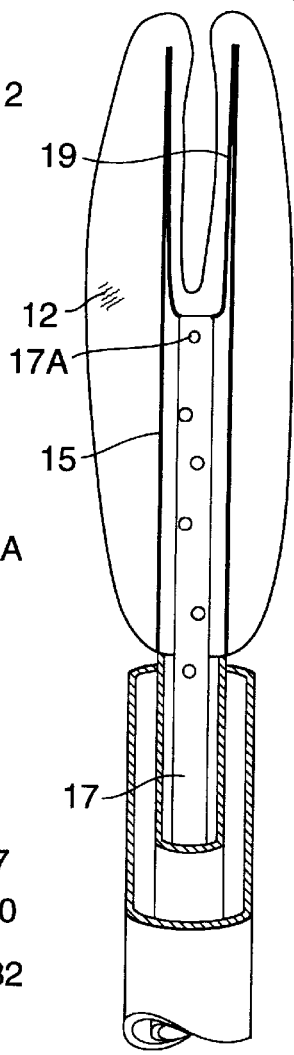
FIG. 9 is a cross-section view of the RF applicator head and the distal portion of the main body of the apparatus of FIG. 1, showing the configuration of RF applicator head after the sheath has been retracted but before the spring members have been released by proximal movement of the shaft.
Figure 10:
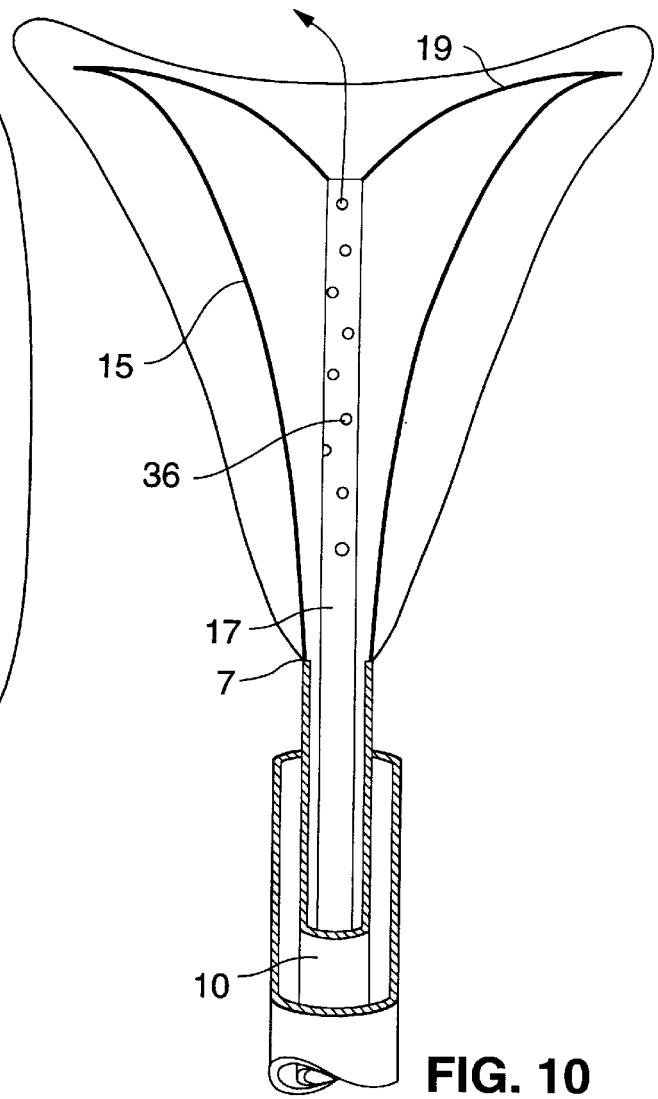
FIG. 10 is a cross-section view of the RF applicator head and the distal portion of the main body of the apparatus of FIG. 1, showing the configuration of RF applicator head after the sheath has been retracted and after the spring members have been released into the fully opened condition.

Referring to FIGS. 1 and 2, an ablation device according to the present invention is comprised generally of three major components: RF applicator head 2, main body 4, and handle 6. Main body 4 includes a shaft 10. The RF applicator head 2 includes an electrode carrying means 12 mounted to the distal end of the shaft 10 and an array of electrodes 14 formed on the surface of the electrode carrying means 12. An RF generator 16 is electrically connected to the electrodes 14 to provide mono-polar or bipolar RF energy to them.

Shaft 10 is an elongate member having a hollow interior. Shaft 10 is preferably 12 inches long and has a preferred cross-sectional diameter of approximately 4 mm. A collar 13 is formed on the exterior of the shaft 10 at the proximal end. As best shown in FIGS. 6 and 7, passive spring member 15 are attached to the distal end of the shaft 10.

Extending through the shaft 10 is a suction/insufflation tube 17 (FIGS. 6–9) having a plurality of holes 17a formed in its distal end. An arched active spring member 19 is connected between the distal ends of the passive spring members 15 and the distal end of the suction/insufflation tube 17.

Referring to FIG. 2, electrode leads 18a and 18b extend through the shaft 10 from distal end 20 to proximal end 22 of the shaft 10. At the distal end 20 of the shaft 10, each of the leads 18a, 18b is coupled to a respective one of the electrodes 14. At the proximal end 22 of the shaft 10, the leads 18a, 18b are electrically connected to RF generator 16 via an electrical connector 21. During use, the leads 18a, 18b carry RF energy from the RF generator 16 to the electrodes. Each of the leads 18a, 18b is insulated and carries energy of an opposite polarity than the other lead.

Electrically insulated sensor leads 23a, 23b (FIGS. 5A and 5B) also extend through the shaft 10. Contact sensors 25a, 25b are attached to the distal ends of the sensor leads 23a, 23b, respectively and are mounted to the electrode carrying means 12. During use, the sensor leads 23a, 23b are coupled by the connector 21 to a monitoring module in the RF generator 16 which measures impedance between the sensors 25a, 25b. Alternatively, a reference pad may be positioned in contact with the patient and the impedance between one of the sensors and the reference pad.

Referring to FIG. 5B, electrode leads 18a, 18b and sensor leads 23a, 23b extend through the shaft 10 between the external walls of the tube 17 and the interior walls of the shaft 10 and they are coupled to electrical connector 21 which is preferably mounted to the collar 13 on the shaft 10. Connector 21, which is connectable to the RF generator 16, includes at least four electrical contact rings 21a–21d (FIGS. 1 and 2) which correspond to each of the leads 18a, 18b, 23a, 23b. Rings 21a, 21b receive, from the RF generator, RF energy of positive and negative polarity, respectively. Rings 21c, 21d deliver signals from the right and left sensors, respectively, to a monitoring module within the RF generator 16.

Referring to FIG. 5A, the electrode carrying means 12 is attached to the distal end 20 of the shaft 10. A plurality of holes 24 may be formed in the portion of the distal end 20 of the shaft which lies within the electrode carrying means 12.

The electrode carrying means 12 preferably has a shape which approximates the shape of the body organ which is to be ablated. For example, the apparatus shown in FIGS. 1 through 11 has a bicornual shape which is desirable for intrauterine ablation. The electrode carrying means 12 shown in these figures includes horn regions 26 which during use are positioned within the cornual regions of the uterus and which therefore extend towards the fallopian tubes.

Electrode carrying means 12 is preferably a sack formed of a material which is non-conductive, which is permeable to moisture and/or which has a tendency to absorb moisture, and which may be compressed to a smaller volume and subsequently released to its natural size upon elimination of compression. Examples of preferred materials for the electrode carrying means include open cell sponge, foam, cotton, fabric, or cotton-like material, or any other material having the desired characteristics. Alternatively, the electrode carrying means may be formed of a metallized fabric. For convenience, the term "pad" may be used interchangeably with the term electrode carrying means to refer to an electrode carrying means formed of any of the above materials or having the listed properties.

Electrodes 14 are preferably attached to the outer surface of the electrode carrying means 12, such as by deposition or other attachment mechanism. The electrodes are preferably made of lengths of silver, gold, platinum, or any other conductive material. The electrodes may be attached to the electrode carrying means 12 by electron beam deposition, or they may be formed into coiled wires and bonded to the electrode carrying member using a flexible adhesive. Naturally, other means of attaching the electrodes, such as sewing them onto the surface of the carrying member, may alternatively be used. If the electrode carrying means 12 is formed of a metallized fabric, an insulating layer may be etched onto the fabric surface, leaving only the electrode regions exposed.

The spacing between the electrodes (i.e. the distance between the centers of adjacent electrodes) and the widths of the electrodes are selected so that ablation will reach predetermined depths within the tissue, particularly when maximum power is delivered through the electrodes (where maximum power is the level at which low impedance, low voltage ablation can be achieved).

The depth of ablation is also effected by the electrode density (i.e., the percentage of the target tissue area which is in contact with active electrode surfaces) and may be regulated by pre-selecting the amount of this active electrode coverage. For example, the depth of ablation is much greater when the active electrode surface covers more than 10% of the target tissue than it is when the active electrode surfaces covers 1% of the target tissue.

For example, by using 3–6 mm spacing and an electrode width of approximately 0.5–2.5 mm, delivery of approximately 20–40 watts over a 9–16 cm$^2$ target tissue area will cause ablation to a depth of approximately 5–7 millimeters when the active electrode surface covers more than 10% of the target tissue area. After reaching this ablation depth, the impedance of the tissue will become so great that ablation will self-terminate as described with respect to the operation of the invention.

By contrast, using the same power, spacing, electrode width, and RF frequency will produce an ablation depth of only 2–3 mm when the active electrode surfaces covers less than 1% of the target tissue area. This can be better understood with reference to FIG. 19A, in which high surface density electrodes are designated 14a and low surface density electrodes are designated 14b. For purposes of this comparison between low and high surface density electrodes, each bracketed group of low density electrodes is considered to be a single electrode. Thus, the electrode widths W and spacings S extend as shown in FIG. 19A.

Figure 19A:
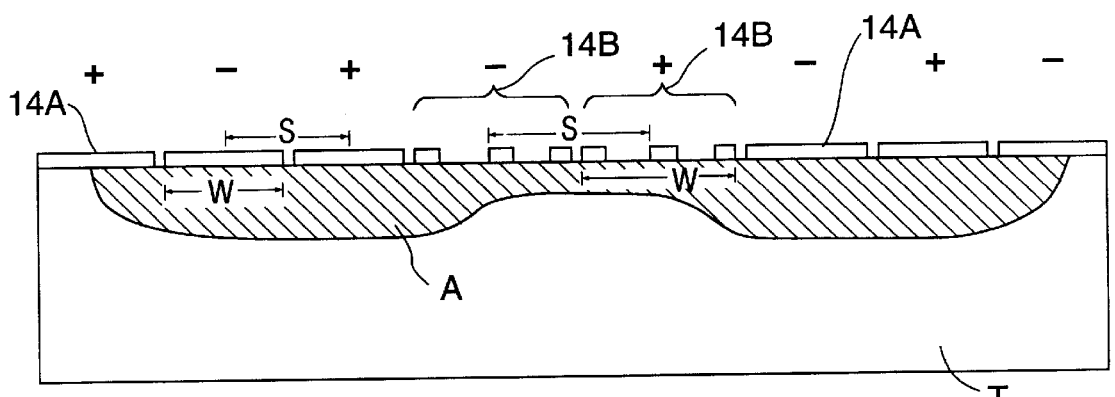
FIGS. 19A–19C are cross-section views of target tissue for ablation, showing electrodes in contact with the tissue surface and illustrating how varying active electrode density may be used to vary the ablation depth.

As is apparent from FIG. 19A, the electrodes 14a, which have more active area in contact with the underlying tissue T, produce a region of ablation A1 that extends more deeply into the tissue T than the ablation region A2 produced by the low density electrodes 14b, even though the electrode spacings and widths are the same for the high and low density electrodes.

Some examples of electrode widths, having spacings with more than 10% active electrode surface coverage, and their resultant ablation depth, based on an ablation area of 6 cm$^2$ and a power of 20–40 watts, are given on the following table:

| ELECTRODE WIDTH | SPACING | APPROX. DEPTH |
|---|---|---|
| 1 mm | 1–2 mm | 1–3 mm |
| 1–2.5 mm | 3–6 mm | 5–7 mm |
| 1–4.5 mm | 8–10 mm | 8–10 mm |

Examples of electrode widths, having spacings with less than 1% active electrode surface coverage, and their resultant ablation depth, based on an ablation area of 6 cm$^2$ and a power of 20–40 watts, are given on the following table:

| ELECTRODE WIDTH | SPACING | APPROX. DEPTH |
|---|---|---|
| 1 mm | 1–2 mm | 0.5–1 mm |
| 1–2.5 mm | 3–6 mm | 2–3 mm |
| 1–4.5 mm | 8–10 mm | 2–3 mm |

Thus it can be seen that the depth of ablation is significantly less when the active electrode surface coverage is decreased.

In the preferred embodiment, the preferred electrode spacing is approximately 8–10 mm in the horn regions 26 with the active electrode surfaces covering approximately 1% of the target region. Approximately 1–2 mm electrode spacing (with 10% active electrode coverage) is preferred in the cervical region (designated 28) and approximately 3–6 mm (with greater than 10% active electrode surface coverage) is preferred in the main body region.

The RF generator 16 may be configured to include a controller which gives the user a choice of which electrodes should be energized during a particular application in order to give the user control of ablation depth. For example, during an application for which deep ablation is desired, the user may elect to have the generator energize every other electrode, to thereby optimize the effective spacing of the electrodes and to decrease the percentage of active electrode surface coverage, as will be described below with respect to FIG. 18.

Although the electrodes shown in the drawings are arranged in a particular pattern, it should be appreciated that the electrodes may be arranged in any pattern to provide ablation to desired depths.

Referring to FIGS. 6 and 7, an introducer sheath 32 facilitates insertion of the apparatus into, and removal of the apparatus from, the body organ to be ablated. The sheath 32 is a tubular member which is telescopically slidable over the shaft 10. The sheath 32 is slidable between a distal condition, shown in FIG. 6, in which the electrode carrying means 12 is compressed inside the sheath, and a proximal condition in which the sheath 32 is moved proximally to release the electrode carrying means from inside it (FIG. 7). By compressing the electrode carrying means 12 to a small volume, the electrode carrying means and electrodes can be easily inserted into the body cavity (such as into the uterus via the vaginal opening).

A handle 34 attached to the sheath 32 provides finger holds to allow for manipulation of the sheath 32. Handle 34 is slidably mounted on a handle rail 35 which includes a sleeve 33, a finger cutout 37, and a pair of spaced rails 35a, 35b extending between the sleeve 33 and the finger cutout 37. The shaft 10 and sheath 32 slidably extend through the sleeve 33 and between the rails 35a, 35b. The tube 17 also extends through the sleeve 33 and between the rails 35a, 35b, and its proximal end is fixed to the handle rail 35 near the finger cutout 37.

A compression spring 39 is disposed around the proximal most portion of the suction/insufflation tube 17 which lies between the rails 35a, 35b. One end of the compression spring 39 rests against the collar 13 on the shaft 10, while the opposite end of the compression spring rests against the handle rail 35. During use, the sheath 32 is retracted from the electrode carrying means 12 by squeezing the handle 34 towards the finger cutout 37 to slide the sheath 32 in the distal direction. When the handle 34 advances against the collar 13, the shaft 10 (which is attached to the collar 13) is forced to slide in the proximal direction, causing compression of the spring 39 against the handle rail 35. The movement of the shaft 10 relative to the suction/insufflation tube 17 causes the shaft 10 to pull proximally on the passive spring member 15. Proximal movement of the passive spring member 15 in turn pulls against the active spring member 19, causing it to move to the opened condition shown in FIG. 7. Unless the shaft is held in this retracted condition, the compression spring 39 will push the collar and thus the shaft distally, forcing the RF applicator head to close. A locking mechanism (not shown) may be provided to hold the shaft in the fully withdrawn condition to prevent inadvertent closure of the spring members during the ablation procedure.

The amount by which the springs 15, 19 are spread may be controlled by manipulating the handle 34 to slide the shaft 10 (via collar 13), proximally or distally. Such sliding movement of the shaft 10 causes forceps-like movement of the spring members 15, 19.

A flow pathway 36 is formed in the handle rail 35 and is fluidly coupled to a suction/insufflation port 38. The proximal end of the suction/insufflation tube 17 is fluidly coupled to the flow pathway so that gas fluid may be introduced into, or withdrawn from the suction/insufflation tube 17 via the suction/insufflation port 38. For example, suction may be applied to the fluid port 38 using a suction/insufflation unit 40. This causes water vapor within the uterine cavity to pass through the permeable electrode carrying means 12, into the suction/insufflation tube 17 via holes 17a, through the tube 17, and through the suction/insufflation unit 40 via the port 38. If insufflation of the uterine cavity is desired, insufflation gas, such as carbon dioxide, may be introduced into the suction/insufflation tube 17 via the port 38. The insufflation gas travels through the tube 17, through the holes 17a, and into the uterine cavity through the permeable electrode carrying member 12.

If desirable, additional components may be provided for endoscopic visualization purposes. For example, lumen 42, 44, and 46 may be formed in the walls of the introducer sheath 32 as shown in FIG. 5B. An imaging conduit, such as a fiberoptic cable 48, extends through lumen 42 and is coupled via a camera cable 43 to a camera 45. Images taken from the camera may be displayed on a monitor 56. An illumination fiber 50 extends through lumen 44 and is coupled to an illumination source 54. The third lumen 46 is an instrument channel through which surgical instruments may be introduced into the uterine cavity, if necessary.

Because during use it is most desirable for the electrodes 14 on the surface of the electrode carrying means 12 to be held in contact with the interior surface of the organ to be ablated, the electrode carrying means 12 may be provide to have additional components inside it that add structural integrity to the electrode carrying means when it is deployed within the body.

Figure 11:
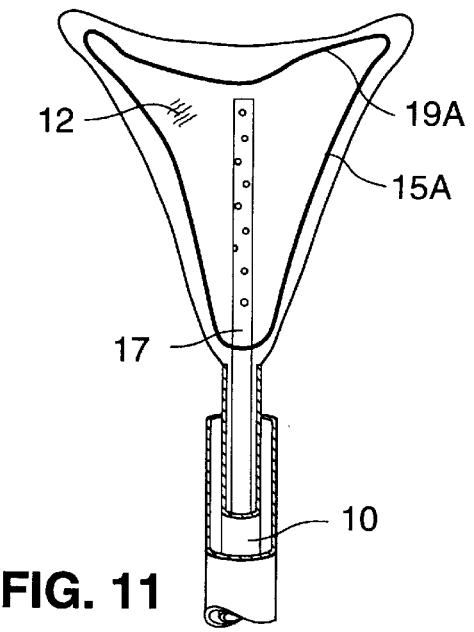
FIG. 11 is a cross-section view of an RF applicator head according to the present invention which utilizes an alternative spring member configuration.

For example, referring to FIG. 11, alternative spring members 15a, 19a may be attached to the shaft 10 and biased such that, when in a resting state, the spring members are positioned in the fully resting condition shown in FIG. 11. Such spring members would spring to the resting condition upon withdrawal of the sheath 32 from the RF applicator head 2.

Figure 20:
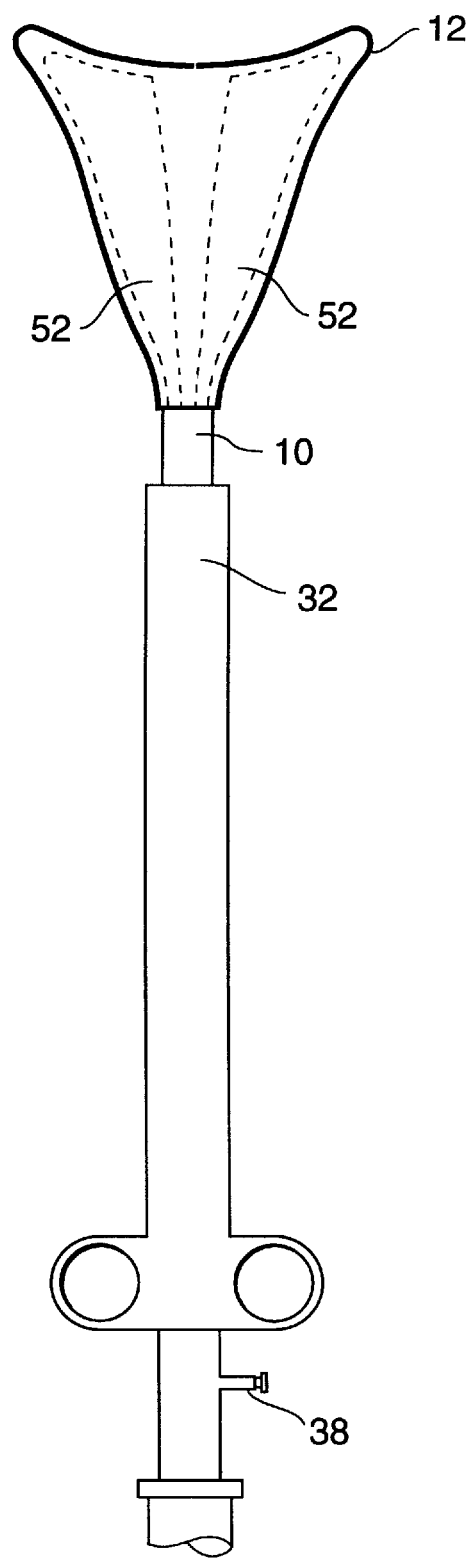
FIG. 20 is a side elevation view, similar to the view of FIG. 2, showing an ablation device according to the present invention in which the electrode carrying means includes inflatable balloons. For purposes of clarity, the electrodes on the electrode carrying means are not shown.

Alternatively, a pair of inflatable balloons 52 may be arranged inside the electrode carrying means 12 as shown in FIG. 20 and connected to a tube (not shown) extending through the shaft 10 and into the balloons 52. After insertion of the apparatus into the organ and following retraction of the sheath 32, the balloons 52 would be inflated by introduction of an inflation medium such as air into the balloons via a port similar to port 38 using an apparatus similar to the suction/insufflation apparatus 40.

Structural integrity may also be added to the electrode carrying means through the application of suction to the proximal end 22 of the suction/insufflation tube 17. Application of suction using the suction/insufflation device 40 would draw the organ tissue towards the electrode carrying means 12 and thus into better contact with the electrodes 14.

Figure 13:
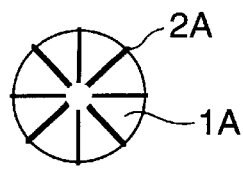
FIG. 13 is a top plan view of the ablation device of FIG. 12.
Figure 14:
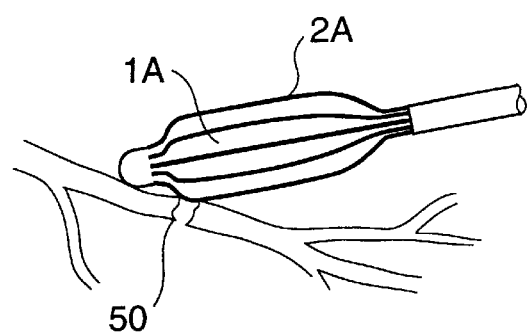
FIG. 14 is a representation of a bleeding vessel illustrating use of the ablation device of FIG. 12 for general bleeding control.
Figure 12:
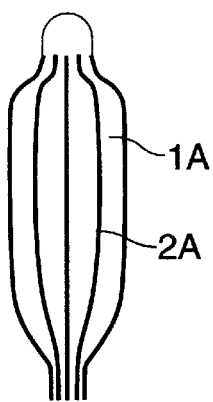
FIG. 12 is a side elevation view of an alternate embodiment of the distal end of an ablation device according to the present invention.
Figure 15:
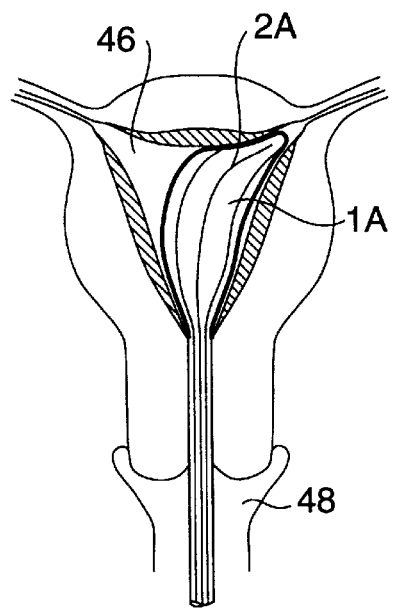
FIGS. 15 and 16 are representations of a uterus illustrating use of the ablation device of FIG. 12 for endometrial ablation.
Figure 16:
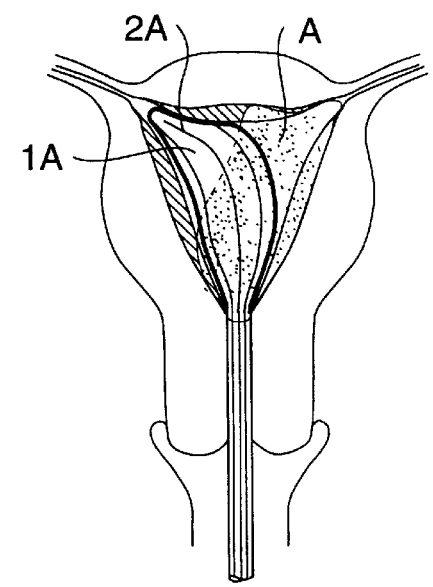
Figure 17:
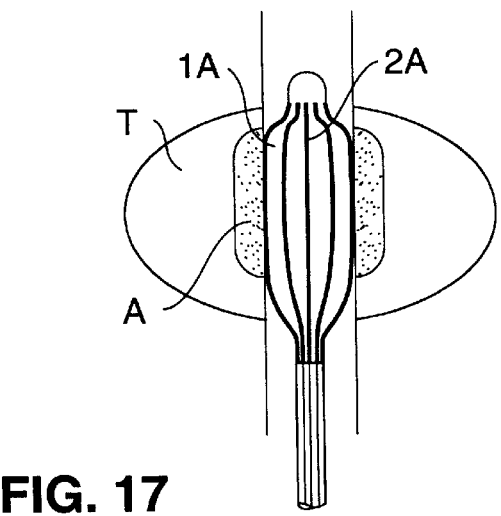
FIG. 17 is a representation of a prostate gland illustrating use of the ablation device of FIG. 12 for prostate ablation.

FIGS. 12 and 13 show an alternative embodiment of an ablation device according to the present invention. In the alternative embodiment, an electrode carrying means 12a is provided which has a shape which is generally tubular and thus is not specific to any particular organ shape. An ablation device having a general shape such as this may be used anywhere within the body where ablation or coagulation is needed. For example, the alternative embodiment is useful for bleeding control during laparoscopic surgery (FIG. 14), tissue ablation in the prostate gland (FIG. 17), and also intrauterine ablation (FIGS. 15 and 16).

Operation

Operation of a preferred ablation device according to the present invention will next be described.

Referring to FIG. 1, the device is initially configured for use by positioning the introducer sheath 32 distally along the shaft 10, such that it compresses the electrode carrying means 12 within its walls.

At this time, the electrical connector 21 is connected to the RF generator 16, and the fiberoptic cable 48 and the illumination cable 50 are connected to the illumination source, monitor, and camera, 54, 56, 45. The suction/insufflation unit 40 is attached to suction/insufflation port 38 on the handle rail 35. The suction/insufflation unit 40 is preferably set to deliver carbon dioxide at an insufflation pressure of 20–200 mmHg.

Next, the distal end of the apparatus is inserted through the vaginal opening V and into the uterus U as shown in FIG. 6, until the distal end of the introducer sheath 32 contacts the fundus F of the uterus. At this point, carbon dioxide gas is introduced into the tube 17 via the port 38, and it enters the uterine cavity, thereby expanding the uterine cavity from a flat triangular shape to a 1–2 cm high triangular cavity. The physician may observe (using the camera 45 and monitor 56) the internal cavities using images detected by a fiberoptic cable 48 inserted through lumen 42. If, upon observation, the physician determines that a tissue biopsy or other procedure is needed, the required instruments may be inserted into the uterine cavity via the instrument channel 46.

Following insertion, the handle 34 is withdrawn until it abuts the collar 13. At this point, the sheath 32 exposes the electrode carrying member 12 but the electrode carrying member 12 is not yet fully expanded (see FIG. 9), because the spring members 15, 19 have not yet been moved to their open condition. The handle 34 is withdrawn further, causing the shaft 10 to move proximally relative to the suction/insufflation tube 17, causing the passive spring members 15 to pull the active spring members 19, causing them to open into the opened condition shown in FIG. 10.

The physician may confirm proper positioning of the electrode carrying member 12 using the monitor 56, which displays images from the fiberoptic cable 48.

Proper positioning of the device and sufficient contact between the electrode carrying member 12 and the endometrium may further be confirmed using the contact sensors 25a, 25b. The monitoring module of the RF generator measures the impedance between these sensors using conventional means. If there is good contact between the sensors and the endometrium, the measured impedance will be approximately 20–180 ohm, depending on the water content of the endometrial lining.

The sensors are positioned on the distal portions of the bicornual shaped electrode carrying member 12, which during use are positioned in the regions within the uterus in which it is most difficult to achieve good contact with the endometrium. Thus, an indication from the sensors 25a, 25b that there is sound contact between the sensors and the endometrial surface indicates that good electrode contact has been made with the endometrium.

Next, insufflation is terminated. Approximately 1–5 cc of saline may be introduced via suction/insufflation tube 17 to initially wet the electrodes and to improve electrode electrical contact with the tissue. After introduction of saline, the suction/insufflation device 40 is switched to a suctioning mode. As described above, the application of suction to the RF applicator head 2 via the suction/insufflation tube 17 collapses the uterine cavity onto the RF applicator head 2 and thus assures better contact between the electrodes and the endometrial tissue.

If the generally tubular apparatus of FIGS. 12 and 13 is used, the device is angled into contact with one side of the uterus during the ablation procedure. Once ablation is completed, the device (or a new device) is repositioned in contact with the opposite side and the procedure is repeated. See FIGS. 15 and 16.

Figure 18:
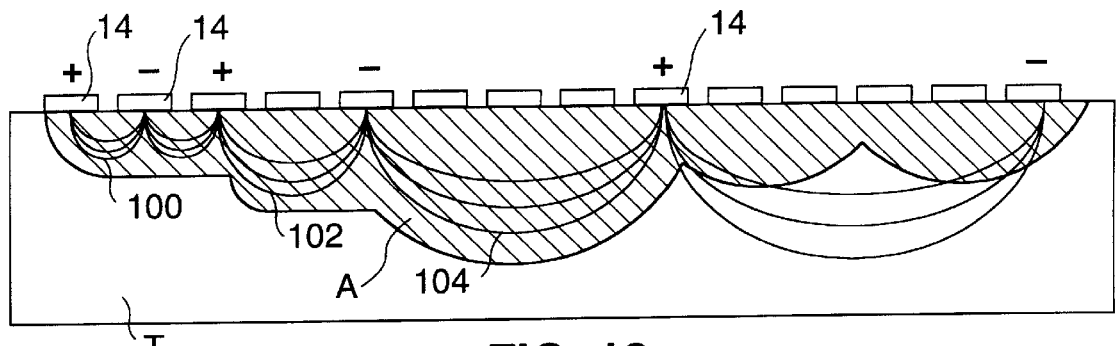
FIG. 18 is a cross-section view of target tissue for ablation, showing ablation electrodes in contact with the tissue surface and illustrating energy fields generated during bi-polar ablation.

Next, RF energy at preferably about 500 kHz and at a constant power of approximately 30 W is applied to the electrodes. As shown in FIG. 5a, it is preferable that each electrode be energized at a polarity opposite from that of its neighboring electrodes. By doing so, energy field patterns, designated 100, 102 and 104 in FIG. 18, are generated between the electrode sites and thus help to direct the flow of current through the tissue T to form a region of ablation A. As can be seen in FIG. 18, if electrode spacing is increased such by energizing, for example every third or fifth electrode rather than all electrodes, the energy patterns will extend more deeply into the tissue. (See, for example, pattern 102 which results from energization of electrodes having a non-energized electrode between them, or pattern 104 which results from energization of electrodes having two non-energized electrodes between them).

Moreover, ablation depth may be controlled as described above by providing low surface density electrodes on areas of the electrode carrying member which will contact tissue areas at which a smaller ablation depth is required (see FIG. 19A).

Figure 19B:
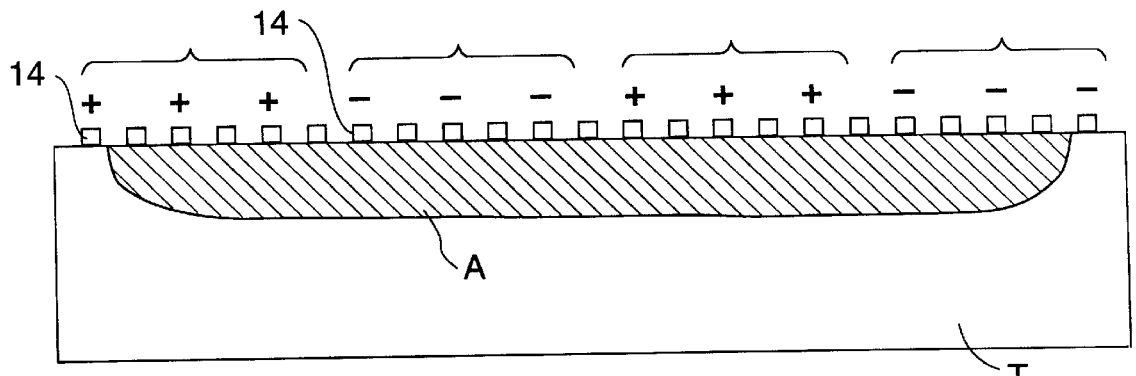

Referring to FIG. 19B, if multiple, closely spaced, electrodes 14 are provided on the electrode carrying member, a user may set the RF generator to energize electrodes which will produce a desired electrode spacing and active electrode area. For example, alternate electrodes may be energized as shown in FIG. 19B, with the first three energized electrodes having positive polarity, the second three having negative polarity, etc.

Figure 19C:
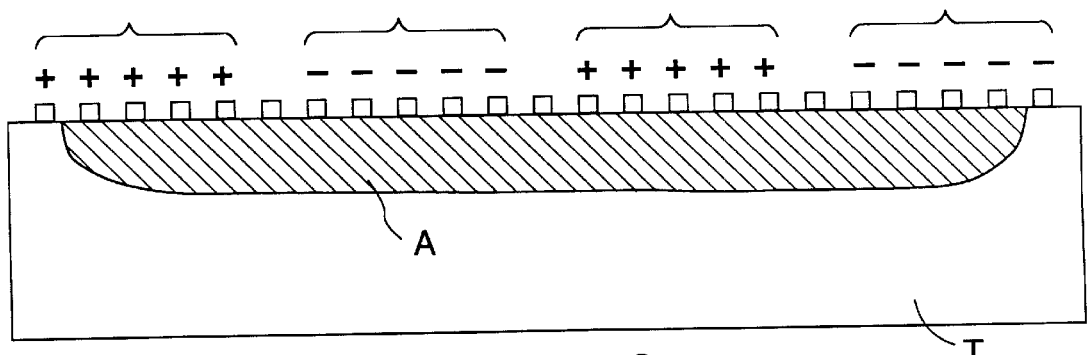

As another example, shown in FIG. 19C, if greater ablation depth is desired the first five electrodes may be positively energized, and the seventh through eleventh electrodes negatively energized, with the sixth electrode remaining inactivated to provide adequate electrode spacing.

As the endometrial tissue heats, moisture begins to be released from the tissue. The moisture permeates the electrode carrying member 12 and is thereby drawn away from the electrodes. The moisture may pass through the holes 17a in the suction/insufflation tube 17 and leave the suction/insufflation tube 17 at its proximal end via port 38 as shown in FIG. 7. Moisture removal from the ablation site may be further facilitated by the application of suction to the shaft 10 using the suction/insufflation unit 40.

Removal of the moisture from the ablation site prevents formation of a liquid layer around the electrodes. As described above, liquid build-up at the ablation site is detrimental in that provides a conductive layer that carries current from the electrodes even when ablation has reached the desired depth. This continued current flow heats the liquid and surrounding tissue, and thus causes ablation to continue by unpredictable thermal conduction means.

Tissue which has been ablated becomes dehydrated and thus decreases in conductivity. By shunting moisture away from the ablation site and thus preventing liquid build-up, there is no liquid conductor at the ablation area during use of the ablation device of the present invention. Thus, when ablation has reached the desired depth, the impedance at the tissue surface becomes sufficiently high to stop or nearly stop the flow of current into the tissue. RF ablation thereby stops and thermal ablation does not occur in significant amounts. If the RF generator is equipped with an impedance monitor, a physician utilizing the ablation device can monitor the impedance at the electrodes and will know that ablation has self-terminated once the impedance rises to a certain level and then remains fairly constant. By contrast, if a prior art bipolar RF ablation device was used together with an impedance monitor, the presence of liquid around the electrodes would cause the impedance monitor to gives a low impedance reading regardless of the depth of ablation which had already been carried out, since current would continue to travel through the low-impedance liquid layer.

Other means for monitoring and terminating ablation may also be provided. For example, a thermocouple or other temperature sensor may be inserted to a predetermined depth in the tissue to monitor the temperature of the tissue and terminate the delivery of RF energy or otherwise signal the user when the tissue has reached a desired ablation temperature.

Once the process has self terminated, 1–5 cc of saline can be introduced via suction/insufflation tube 17 and allowed to sit for a short time to aid separation of the electrode from the tissue surface. The suction/insufflation device 40 is then switched to provide insufflation of carbon dioxide at a pressure of 20–200 mmHg. The insufflation pressure helps to lift the ablated tissue away from the RF applicator head 2 and to thus ease the closing of the RF applicator head. The RF applicator head 2 is moved to the closed position by sliding the handle 34 in a distal direction to fold the spring members 15, 19 along the axis of the device and to cause the introducer sheath 32 to slide over the folded RF applicator head. The physician may visually confirm the sufficiency of the ablation using the monitor 56. Finally, the apparatus is removed from the uterine cavity.

We claim:

1. An ablation and/or coagulation apparatus for use in delivering energy to tissue for ablation, the apparatus comprising:

a moisture permeable and/or absorbable electrode carrying member configured to permit moisture generated during ablation to pass into the electrode carrying member and away from underlying tissue;

electrodes mounted to the electrode carrying member; and means for delivering radio frequency energy to the electrodes.

2. The apparatus of claim 1 wherein the electrode carrying member is formed of sponge.

3. The apparatus of claim 1 wherein the electrode carrying member is formed of foam.

4. The apparatus of claim 1 wherein the electrode carrying member is formed of a porous filler material.

5. The apparatus of claim 1 wherein the electrode carrying member is further formed of conformable material.

6. The ablation apparatus of claim 1 further comprising structural support means within the electrode carrying member.

7. The ablation apparatus of claim 6 wherein the structural support means includes an inflatable balloon.

8. The ablation apparatus of claim 6 wherein the structural support means comprises spring members positioned within the electrode carrying member.

9. The ablation apparatus of claim 8 wherein the spring members are moveable between a closed condition and an opened condition.

10. The ablation apparatus of claim 1 further comprising at least one contact sensor carried by the electrode carrying member and means for measuring impedance.

11. A method of ablating and/or coagulating tissue, comprising the steps of:

(a) providing an electrode carrying member with electrodes thereon;

(b) positioning the electrodes in contact with tissue to be ablated;

(c) passing current through the electrodes to the tissue to cause the tissue to dehydrate; and (d) permitting moisture generated during the dehydration of step (c) to pass into the electrode carrying member and away from the tissue.

12. The method of claim 11 wherein the tissue has a surface and wherein step (b) includes the step of causing the electrode carrying member to conform to the shape of the tissue surface.

13. The method of claim 11 wherein the method further includes the step of (e) automatically terminating the flow of current into the tissue once ablation has approximately reached a predetermined depth or level of dehydration.

14. The method of claim 11 wherein the method further includes the steps of:

(e) monitoring the impedance of the tissue undergoing ablation; and (f) terminating the ablation procedure once the impedance has reached a predetermined level.

15. The method of claim 11 wherein step (c) includes the step of passing current through select ones of the electrodes.

16. The method of claim 11 including the step of applying suction through the electrode carrying means to draw the tissue into contact with the electrode carrying means and the electrodes to facilitate moisture removal.

17. A method of ablating and/or coagulating tissue, comprising the steps of:

(a) providing an elongate tube and providing an electrode carrying member with electrodes thereon on a distal portion of the tube;

(b) positioning the electrodes in contact with tissue to be ablated;

(c) passing current through the electrodes to the tissue to cause the tissue to dehydrate; and (d) permitting moisture generated during the dehydration of step (c) to pass into the electrode carrying member and away from the tissue and permitting at least a portion of the moisture to pass from the electrode carrying member through the tube.

18. The method of claim 17 wherein step (d) includes the step of applying suction to the tube to draw the moisture through the tube.

19. An ablation and/or coagulation apparatus for use in delivering energy to tissue for ablation, the apparatus comprising:

an elongate tube;

a moisture permeable and/or absorbable electrode carrying member mounted to the tube, the tube including a plurality of aeration openings underlying the electrode carrying member;

electrodes mounted to the electrode carrying member; and means for delivering radio frequency energy to the electrodes.

20. An ablation and/or coagulation apparatus for use in delivering energy to tissue for ablation, the apparatus comprising:

a moisture permeable and/or absorbable electrode carrying member;

electrodes mounted to the electrode carrying member;

means for delivering radio frequency energy to the electrodes; and suction means for drawing moisture away from the electrode carrying member.

21. An ablation and/or coagulation apparatus for use in delivering energy to tissue for ablation, the apparatus comprising:

an elongate tube;

a moisture permeable and/or absorbable electrode carrying member mounted to the tube;

electrodes mounted to the electrode carrying member;

means for delivering radio frequency energy to the electrodes; and suction means for drawing moisture through the tube away from the electrode carrying member.

22. An apparatus for intrauterine ablation, comprising:

an elongate tube;

an electrode carrying pad mounted to the tube and shaped to approximate the shape of a uterus;

an array of electrodes mounted to the pad;

means for delivering RF energy to the electrodes to cause current flow from the electrodes to tissue to be ablated; and means for automatically terminating the flow of current from the electrodes to the tissue once a predetermined ablation depth has been substantially reached.

23. The apparatus of claim 22 further comprising means for drawing moisture from tissue undergoing ablation into the electrode carrying pad.

24. A method of ablating tissue, comprising the steps of:
(a) providing an electrode carrying member with electrodes thereon;
(b) positioning the electrodes in contact with tissue to be ablated;
(c) selecting a depth to which ablation is to be carried out; and
(d) delivering RF energy to the tissue through select ones of the electrodes to cause ablation of the tissue to approximately the selected ablation depth and to cause automatic termination of current flow into the tissue once the selected ablation depth has been approximately reached.

25. A method of ablating tissue, comprising the steps of:
(a) providing an electrode carrying member with electrodes thereon;
(b) positioning the electrodes in contact with tissue to be ablated;
(c) selecting a depth to which ablation is to be carried out; and
(d) selecting an effective electrode spacing which would produce ablation to approximately the desired ablation depth, and delivering RF energy to select ones of the electrodes such that the spacing between the energized electrodes is substantially the selected effective electrode spacing, to cause ablation of the tissue to approximately the selected ablation depth.

26. A method of ablating tissue, comprising the steps of:
(a) providing an electrode carrying member with electrodes thereon;
(b) positioning the electrodes in contact with tissue to be ablated;
(c) selecting a depth to which ablation is to be carried out; and
(d) selecting an electrode surface density which will produce ablation to approximately the desired ablation depth, and delivering RF energy to select ones of the electrodes such that the electrode surface density of the energized electrodes is substantially the selected electrode surface density, to cause ablation of the tissue to approximately the selected ablation depth.

27. An ablation and/or coagulation apparatus for use in delivering energy to tissue for ablation, the apparatus comprising:
an electrode member formed of a metallized fabric having insulating regions formed thereon; and
a source of RF energy electrically coupled to the metallized fabric.

28. The apparatus of claim 27 wherein the electrode member is mounted to an elongate member.

29. The apparatus of claim 28 wherein the elongate member is tubular.

30. The apparatus of claim 27 wherein the metallized fabric is moisture permeable.

31. The apparatus of claim 30 further comprising a vacuum source fluidly coupled to the electrode member to actively draw moisture away from underlying tissue.

32. The apparatus of claim 31 wherein the electrode member is mounted to an elongate tubular member and wherein the vacuum source is fluidly coupled to the electrode member to actively draw moisture away from underlying tissue and into the elongate tubular member.

33. The apparatus of claim 27 wherein the insulating regions are etched onto the metallized fabric.

* * * * *

UNITED STATES PATENT AND TRADEMARK OFFICE
CERTIFICATE OF CORRECTION

PATENT NO. : 5,769,880 C1
DATED : August 24, 2004
INVENTOR(S) : Csaba Truckai et al.

It is certified that error appears in the above-identified patent and that said Letters Patent is hereby corrected as shown below:

Title page,
Item [56], References Cited, U.S. PATENT DOCUMENTS, please add the following references:

-- 5,277,201    1/1994 Stern ............... 128/788
    5,383,917    1/1995 Desai et al. ........ 607/102 --; and OTHER PUBLICATIONS, please add the following references:

-- Haines & Verow, "Observations on Electrode Tissue Interface Temperature and Effect on Electrical Impedance During Radiofrequency Ablation of Ventricular Myocardium"; Circulation, 82:3, Sept '90, pp. 1034-1038. --.

-- Nibley et al.: Abstract of "Prevention of Impedance Rise During Radiofrequency Current by Intra-Electrode Tip Chilling"; Circulation, 90:4, part 2; Oct. '94, p. I-271. --.

-- Jackman et al.: "Radiofrequency Current Directed Across the Mitral Anulus with a Bipolar Epicardial–Endocardial Catheter Electrode Configuration in Dogs"; Circulation, 78:5, Nov. '88. --.

Signed and Sealed this

Twenty-seventh Day of September, 2005

JON W. DUDAS
*Director of the United States Patent and Trademark Office*

(12) EX PARTE REEXAMINATION CERTIFICATE (4979th)
United States Patent
Truckai et al.

(10) Number: US 5,769,880 C1
(45) Certificate Issued: Aug. 24, 2004

(54) MOISTURE TRANSPORT SYSTEM FOR CONTACT ELECTROCOAGULATION

(75) Inventors: Csaba Truckai, Sunnyvale, CA (US); David C. Auth, Kirkland, WA (US)

(73) Assignee: Novacept, Palo Alto, CA (US)

Reexamination Request:
No. 90/005,435, Jul. 27, 1999
No. 90/005,866, Nov. 22, 2000

Reexamination Certificate for:
Patent No.: 5,769,880
Issued: Jun. 23, 1998
Appl. No.: 08/632,516
Filed: Apr. 12, 1996

(51) Int. Cl.$^7$ .............................. A61F 2/00; A61F 7/00; A61F 7/12; A61N 1/00; A61N 1/30; A61M 31/00
(52) U.S. Cl. .................... 607/101; 607/99; 607/116; 604/20; 604/49; 604/55; 604/114
(58) Field of Search ........................... 604/20, 21, 500, 604/503, 509, 114, 96; 606/27–29, 31, 32, 41, 46–50, 191–193; 607/96, 101, 102, 113, 116, 138

(56) References Cited

U.S. PATENT DOCUMENTS

| | | | |
|---|---|---|---|
| 552,832 A | 1/1896 | Fort | |
| 725,731 A | 4/1903 | Linn | |
| 1,620,929 A | 3/1927 | Wallerich | |
| 3,228,398 A | 1/1966 | Leonard et al. | 128/269 |
| 3,324,855 A | 6/1967 | Heimlich | 128/269 |
| 3,877,464 A | 4/1975 | Vermes | 128/2 B |
| 3,971,378 A | 7/1976 | Krantz | 128/285 |
| 4,022,215 A | 5/1977 | Benson | 128/303.1 |
| 4,082,096 A | 4/1978 | Benson | 128/303.1 |
| 4,233,025 A | 11/1980 | Larson et al. | 433/136 |
| 4,415,288 A | 11/1983 | Gordon et al. | 401/132 |
| 4,465,072 A | 8/1984 | Taheri | 128/348.1 |
| 4,568,326 A | 2/1986 | Rangaswamy | 604/1 |
| 4,628,924 A | 12/1986 | Cimber | 128/130 |
| 4,765,331 A | 8/1988 | Petruzzi et al. | 128/303.14 |
| 4,946,440 A | 8/1990 | Hall | 604/95 |
| 4,981,465 A | 1/1991 | Ballan et al. | 600/32 |
| 4,983,177 A | 1/1991 | Wolf | 606/157 |
| 5,065,751 A | 11/1991 | Wolf | 128/831 |
| 5,078,717 A | 1/1992 | Parins et al. | 606/48 |
| 5,084,044 A | 1/1992 | Quint | |
| 5,354,295 A | 10/1994 | Guglielmi et al. | 606/32 |
| 5,374,261 A | 12/1994 | Yoon | |
| 5,395,311 A | 3/1995 | Andrews | 604/22 |
| 5,443,470 A | 8/1995 | Stern et al. | |
| 5,505,730 A | 4/1996 | Edwards | |
| 5,514,091 A | 5/1996 | Yoon | 604/101 |
| 5,562,703 A * | 10/1996 | Desai | 606/210 |
| 5,613,950 A | 3/1997 | Yoon | 604/105 |
| 5,656,013 A | 8/1997 | Yoon | 600/207 |
| 5,667,520 A | 9/1997 | Bonutti | 606/190 |

(List continued on next page.)

FOREIGN PATENT DOCUMENTS

| | | | |
|---|---|---|---|
| DE | 384246 | 10/1923 | |
| EP | 0056178 | 7/1982 | |
| FR | 774.550 | 12/1934 | 19/1 |
| FR | 70.43012 | 7/1972 | |
| JP | 48-67586 | 8/1973 | |
| JP | 58-32756 | 2/1983 | A61B/17/22 |
| JP | 63-318934 | 12/1988 | A61B/17/36 |
| WO | WO 94/00178 | 6/1994 | A61M/29/00 |

Primary Examiner—Michael J. Hayes

(57) ABSTRACT

An apparatus and method for use in performing ablation of organs and other tissue includes an electrode carrying member which is substantially absorbent and/or permeable to moisture. The electrode carrying member is mounted to the distal end of an elongate shaft, and an array of electrodes is mounted to the surface of the electrode carrying member. Following placement of the ablation device into contact with the tissue to be ablated, an RF generator is used to deliver RF energy to the electrodes and to thereby induce current flow from the electrodes to tissue to be ablated. As the current heats the tissue, moisture (such as water vapor or liquid) leaves the tissue causing the tissue to dehydrate. The moisture permeability and/or absorbency of the electrode carrying member allows the moisture to leave the ablation site so as to prevent the moisture from providing a path of conductivity for the current.

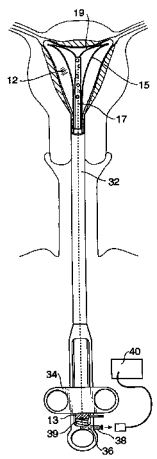

U.S. PATENT DOCUMENTS

| | | | | |
|---|---|---|---|---|
| 5,697,882 A | * | 12/1997 | Eggers et al. | 604/114 |
| 5,702,438 A | | 12/1997 | Avitall | 607/122 |
| 5,716,343 A | | 2/1998 | Kriesel et al. | 604/132 |
| 5,730,725 A | | 3/1998 | Yoon | 604/101 |
| 5,779,698 A | | 7/1998 | Clayman et al. | 606/39 |
| 5,797,903 A | | 8/1998 | Swanson et al. | 606/34 |
| 5,800,482 A | * | 9/1998 | Pomeranz et al. | 607/101 |
| 5,846,238 A | | 12/1998 | Jackson et al. | 606/41 |
| 5,871,469 A | | 2/1999 | Eggers et al. | 604/114 |
| 5,879,348 A | | 3/1999 | Owens et al. | 606/41 |
| 5,888,198 A | | 3/1999 | Eggers et al. | 604/114 |
| 5,891,134 A | | 4/1999 | Goble et al. | 606/27 |
| 5,891,136 A | | 4/1999 | McGee et al. | 606/41 |
| 5,897,553 A | * | 4/1999 | Mulier et al. | 606/41 |
| 6,002,968 A | * | 12/1999 | Edwards | 607/101 |
| 6,042,596 A | | 3/2000 | Bonutti | 606/190 |
| 6,068,613 A | | 5/2000 | Kriesel et al. | 604/132 |
| 6,277,089 B1 | | 8/2001 | Yoon | 604/1 |
| 6,395,012 B1 | | 5/2002 | Yoon et al. | 606/193 |
| 6,475,213 B1 | | 11/2002 | Whayne et al. | 606/34 |

* cited by examiner

US 5,769,880 C1

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 6, lines 23–30:

In the preferred embodiment, the preferred electrode spacing is approximately 8–10 mm in the horn regions 26 with the active electrode surfaces covering approximately 1% of the target region. Approximately 1–2 mm electrode spacing (with 10% active electrode coverage) is preferred in the cervical region (designated 28) and approximately 3–6 mm (with greater than 10% active electrode surface coverage) is preferred in the main body region *29*.

Column 10, lines 19–26:

Removal of the moisture from the ablation site prevents formation of a liquid layer around the electrodes. As described above, liquid build-up at the ablation site is detrimental in that *it* provides a conductive layer that carries current from the electrodes even when ablation has reached the desired depth. This continued current flow heats the liquid and surrounding tissue, and thus causes ablation to continue by unpredictable thermal conduction means.

AS A RESULT OF REEXAMINATION, IT HAS BEEN DETERMINED THAT:

Claims 2, 3, 17, 18 and 23 are cancelled.

Claims 1, 4, 11, 13, 16, 19–22 and 24–27 are determined to be patentable as amended.

Claims 5–10, 12, 14, 15 and 28–33, dependent on an amended claim, are determined to be patentable.

New claims 34–103 are added and determined to be patentable.

1. An ablation and/or coagulation apparatus for use in delivering energy to *uterine* tissue for ablation, the apparatus comprising:
   a moisture permeable [and/or absorbable] electrode carrying member *which does not have a tendency to absorb moisture and which* is configured to permit moisture generated during ablation to pass into the electrode carrying member and away from underlying tissue, *the electrode carrying member having a bicornal shape to approximate the interior shape of a uterus;*
   *a bipolar array of* electrodes mounted to the electrode carrying member; [and]
   means for delivering radio frequency energy to the electrodes*; and*
   suction means for drawing moisture released by tissue undergoing ablation through and away from the electrode carrying member and for substantially preventing formation of a low-impedance liquid layer around the electrodes when ablation/coagulation is carried out using the electrodes.

4. The apparatus of claim 1 wherein the electrode carrying member is formed of a [porous filler material] *fabric metallized with a conductive metal, said metallized fabric* having non-conductive regions formed thereon to divide the electrode carrying member into the bi-polar array of electrodes.

11. A method of ablating and/or coagulating tissue, comprising the steps of:
   (a) providing an electrode carrying member with *an array of bipolar* electrodes thereon, *the electrode carrying member shaped to approximate the shape of a uterus*;
   (b) *inserting the electrode carrying member into a uterus and* positioning the electrodes in contact with tissue to be ablated;
   (c) passing current through the electrodes to the tissue to cause the tissue to [dehydrate] *ablate and/or coagulate*; and
   (d) [permitting] *during ablation and/or coagulation of the tissue, applying suction through the electrode carrying member to draw* moisture generated during the [dehydration of step (c) to pass] *ablation and/or coagulation* into the electrode carrying member and away from the tissue *and electrodes, said suction substantially preventing formation of a low-impedance liquid layer around the electrodes when ablation/coagulation is carried out using the electrodes*.

13. The method of claim 11 wherein the method further includes the step of
   (e) automatically terminating the flow of current into the tissue once ablation has approximately reached a predetermined depth or level of [dehydration] *ablation and/or coagulation*.

16. [The] *A* method of [claim 11 including the step of] *ablating and/or coagulating tissue, comprising the steps of*:
   (*a*) *providing an electrode carrying member formed of a fabric metallized with a conductive metal, said metallized fabric having non-conductive regions formed thereon to create a bipolar array of electrodes;*
   (*b*) *positioning the electrodes in contact with tissue to be ablated;*
   (*c*) *passing current through the electrodes to the tissue to cause the tissue to ablate and/or coagulate; and*
   (*d*) applying suction through the electrode carrying [means] *member* to draw the tissue into contact with the electrode carrying means and the electrodes [to facilitate moisture removal] *and to draw moisture generated during the ablation and/or coagulation into the electrode carrying member and away from the tissue and electrodes, said suction substantially preventing formation of a low-impedance liquid layer around the electrodes when ablation/coagulation is carried out using the electrodes*.

19. An ablation and/or coagulation apparatus for use in delivering energy to tissue for ablation, the apparatus comprising:
   an elongate tube;
   a moisture permeable [and/or absorbable] electrode carrying member mounted to the tube, *the electrode carrying member formed of an envelope of moisture permeable material which does not have a tendency to absorb moisture, said envelope having a hollow interior and a bicornal shape which approximates the* shape of the uterus, the tube including a plurality of aeration openings underlying the electrode carrying member;

electrodes mounted to the electrode carrying member; [and]

means for delivering radio frequency energy to the electrodes; and suction means for drawing moisture released by tissue undergoing ablation through and away from the electrode carrying member and through the aeration openings and for substantially preventing formation of a low-impedance liquid layer around the electrodes when ablation/coagulation is carried out using the electrodes.

20. An ablation and/or coagulation apparatus for use in delivering energy to tissue for ablation, the apparatus comprising:

[a moisture permeable and/or absorbable electrode carrying member;

electrodes mounted to the electrode carrying member;]

*an envelope of moisture permeable material having a hollow interior, said material comprising a fabric metallized with a conductive metal, said metallized fabric having non-conductive regions formed thereon to create and array of electrodes, said envelope shaped to approximate the interior shape of a uterus;* means for delivering radio frequency energy to the electrodes; and suction means for drawing moisture *generated during ablation/coagulation of tissue into the hollow interior and* away from the [electrode carrying member] *envelope and for substantially prevention formation of a low-impedance liquid layer around the electrodes.*

21. An ablation and/or coagulation apparatus for use in delivering energy to tissue for ablation, the apparatus comprising:

an elongate tube;

a moisture permeable [and/or absorbable] electrode carrying member mounted to the tube[;

electrodes mounted to the electrode carrying member]*, said electrode carrying member comprising a fabric metallized with a conductive metal, said metallized fabric having non-conductive regions thereon to create a bipolar array of electrodes separated by the non-conductive regions*;

means for delivering radio frequency energy to the electrodes; and suction means for drawing moisture *generated during ablation/coagulation* through the tube away from the electrode carrying member *and for substantially preventing formation of a low-impedance liquid layer around the electrodes.*

22. An apparatus for intrauterine ablation, comprising:

an elongate tube;

[an] *a moisture permeable* electrode carrying [pad] *member* mounted to the tube and shaped to approximate the shape of a uterus[;

an array of electrodes mounted to the pad]*, the electrode carrying member comprising a fabric metallized with a conductive metal, said metallized fabric having non-conductive regions formed thereon to create an array of bipolar electrodes*;

*RF energy* means for delivering RF energy to the electrodes to cause current flow from the electrodes to tissue to be ablated; and

[means for automatically terminating the flow of current from the electrodes to the tissue once a predetermined ablation depth has been substantially reached]

*vacuum means operable during RF delivery to the electrodes, said vacuum means for applying a vacuum through the moisture permeable electrode member to draw moisture released by tissue undergoing ablation through the moisture permeable electrode, for thereby substantially preventing the released moisture from creating a layer of liquid which can provide an electrically conductive pathway between the electrodes, for thus allowing a rise of impedance at the electrodes that corresponds to the rise impedance of the tissue, and for thereby causing flow of energy through the electrodes to terminate once dehydration of the tissue has approximately reached a desired ablation depth.*

24. A method of ablating tissue, comprising the steps of:

(a) providing an electrode carrying member with electrodes thereon;

(b) positioning the electrodes in contact with tissue to be ablated;

(c) selecting a depth to which ablation is to be carried out, *said depth selected from plurality of depths to which the electrode carrying member is configured to ablate*; [and]

(d) *selecting a combination of electrodes that, when energized with RF energy, will deliver current to the tissue in a manner that causes ablation of the tissue to approximately the selected ablation depth and that further causes automatic termination of current flow into the tissue once the selected ablation depth has been approximately reached; and*

(e) delivering RF energy to the tissue through [select ones] *the selected combination* of the electrodes to cause ablation of the tissue to approximately the selected ablation depth and to cause automatic termination of current flow into the tissue once the selected ablation depth has been approximately reached *said termination occurring regardless of whether RF energy continues to be delivered to the selected combination of the electrodes; and*

(f) *during step (e), applying suction to draw moisture away from the electrode carrying member thereby substantially preventing a layer of low-impedance liquid from forming around the electrodes during ablation.*

25. A method of ablating tissue, comprising the steps of:

(a) providing an electrode carrying member with electrodes *of a known width* thereon;

(b) positioning the electrodes in contact with tissue to be ablated;

(c) selecting a depth to which ablation is to be carried out; and (d) *after step (c),* selecting an effective electrode spacing which would produce ablation to approximately the [desired] *selected* depth *and known to cause automatic termination of current flow into the tissue once the selected* ablation depth *has been approximately reached regardless of whether RF energy continues to be delivered to the electrodes*, and *selectively* delivering RF energy to [select ones of the electrodes such that the spacing between the energized electrodes is substantially the] *electrodes spaced-apart by said* selected effective electrode spacing, to cause ablation of the tissue to approximately the selected ablation depth *and* to cause automatic termination of current flow into the tissue once the selected ablation depth has been approximately reached, said termination occurring regardless of whether RF energy continues to be delivered to the select ones of the electrodes.

26. A method of ablating tissue, comprising the steps of:
(a) providing an electrode carrying member with electrodes thereon;
(b) positioning the electrodes in contact with tissue to be ablated;
(c) selecting a depth to which ablation is to be carried out; and
(d) *after step (c),* selecting an electrode surface density [which will] *known to* produce ablation to approximately the [desired] *selected depth and known to cause automatic termination of current flow into the tissue once the selected* ablation depth *has been approximately reached regardless of whether RF energy continues to be delivered to the electrodes,* and *selectively* delivering RF energy to [select ones of the] electrodes *having said selected electrode surface density, to cause ablation of the tissue to approximately the selected ablation depth, and to cause automatic termination of current flow into the tissue once the selected ablation depth has been approximately reached, said termination occurring regardless of whether RF energy continues to be delivered to the* electrodes [such that the electrode surface density of the energized electrodes is substantially the selected electrode surface density, to cause ablation of the tissue to approximately the selected ablation depth] *is having the selected surface density*.

27. An ablation and/or coagulation apparatus for use in delivering energy to tissue for ablation, the apparatus comprising:
an electrode member formed of a metallized fabric having insulating regions formed thereon *to create an electrode array*; [and]
a source of RF energy electrically coupled to the *electrode array;* and
a vacuum source operable during delivery of RF energy from the electrode array to body tissue in contact with the electrode array, the vacuum source for drawing moisture relased by body tissue through *the* metallized fabric *and away from the electrodes to prevent formation of a low-impedance liquid layer around the electrodes*.

34. The apparatus of claim 27 wherein the electrode member is shaped to approximate the shape of a uterus.

35. The method of claim 16 wherein step (a) further provides a flexible support within the electrode carrying member, wherein step (b) includes positioning the electrode carrying member within a body cavity, and wherein the method further includes the step of substantially conforming the electrode carrying member to the shape of the body cavity using the structural support and the suction applied in step (e).

36. The method of claim 16 wherein the electrode carrying member is shaped to approximate the shape of a uterus, and wherein step (b) includes the step of inserting the electrode carrying member into a uterus.

37. The apparatus of claim 19 wherein the electrodes and the electrode carrying member together comprise the envelope.

38. The apparatus of claim 21 wherein the electrode carrying member is shaped to approximate the shape of a uterus.

39. The apparatus of claim 22 wherein the electrode carrying member is formed of an envelope of the metallized fabric, said envelope having a hollow interior.

40. The method of claim 24 wherein step (a) provides and electrode carrying member with a bipolar array of electrodes thereon.

41. The method of claim 24 wherein the electrode carrying member is shaped to approximate the shape of a uterus, and wherein step (b) includes the step of inserting the electrode carrying member into a uterus.

42. The method of claim 25 wherein step (a) provides an electrode carrying member with a bipolar array of electrodes thereon.

43. The method of claim 26 wherein step (a) provides an electrode carrying member with a bipolar array of electrodes thereon.

44. An ablation and/or coagulation apparatus for use in delivering energy to tissue for ablation, the apparatus comprising:
a moisture permeable electrode carrying member, said member formed of fabric metallized with a conductive material and having non-conductive regions formed thereon to create a bipolar array of electrodes;
means for delivering radio frequency energy to the electrodes to cause current to flow from the electrodes to tissue in contact with the electrodes during an ablation/coagulation procedure; and
suction means for drawing moisture generated during ablation/coagulation of tissue through the metallized fabric and away from the electrode carrying member and for substantially preventing formation of a low-impedance liquid layer around the electrodes during an ablation/coagulation procedure.

45. The apparatus of claim 44 wherein the electrode carrying member is formed of an envelope of the metallized fabric.

46. The apparatus of claim 44 further comprising a structural support within the electrode carrying member.

47. The apparatus of claim 46 wherein the structural support includes spring members positioned within the electrode carrying member.

48. The apparatus of claim 47 wherein the spring members are moveable between a closed condition and an opened condition.

49. The apparatus of claim 44 wherein the electrode carrying member is shaped to approximate the shape of a uterus.

50. An ablation and/or coagulation apparatus for use in delivering energy to tissue for ablation, the apparatus comprising:
an electrode carrying member formed of an envelope of moisture permeable material having a hollow interior, said material formed of fabric metallized with a conductive material and having non-conductive regions formed thereon to create an array of electrodes;
means for delivering radio frequency energy to the electrodes to cause current to flow from electrodes to tissue in contact with the electrodes during an ablation/coagulation procedure; and
suction means for drawing moisture generated during ablation/coagulation of tissue into the hollow interior away from the tissue and for substantially preventing formation of a low-impedance liquid layer around the electrodes during an ablation/coagulation procedure.

51. The apparatus of claim 50 wherein the non-conductive regions separate the electrode carrying member into an array of bi-polar electrodes.

52. The apparatus of claim 51 further comprising a structural support within the electrode carrying member.

53. The apparatus of claim 52 wherein the structural support includes spring members positioned within the hollow interior of the electrode carrying member.

54. The apparatus of claim 53 wherein the spring members are moveable between a closed condition and an opened condition.

55. The apparatus of claim 50 wherein the electrode carrying member is shaped to approximate the shape of a uterus.

56. An ablation and/or coagulation apparatus for use in delivering energy to tissue for ablation, the apparatus comprising:

an electrode carrying member having a first electrode region and a second electrode region;

electrodes formed on the electrode carrying member in the first and second electrode regions, the electrodes in the first electrode region having a first electrode spacing selected to carry out ablation/coagulation to a first depth, the electrodes in the second electrode region having a second electrode spacing different than the first electrode spacing, the second electrode spacing selected to carry out ablation/coagulation to a second depth;

means for delivering radio frequency energy to the electrodes; and suction means for drawing moisture generated during ablation/coagulation of tissue away from the electrode carrying member and for substantially preventing formation of a low-impedance liquid layer around the electrodes.

57. The apparatus of claim 56 wherein the electrode carrying member is shaped to approximate the shape of a human uterus and includes a horn region, a main body region, and a cervical region, and wherein the first electrode region is the horn region and the second electrode region is the main body region.

58. The apparatus of claim 56 wherein the electrode carrying member is shaped to approximate the shape of a human uterus and includes a horn region, a main body region, and a cervical region, and wherein the first electrode region is the cervical region and the second electrode region is the main body region.

59. The apparatus of claim 56 wherein the electrode carrying member is shaped to approximate the shape of a human uterus and includes a horn region, a main body region, and a cervical region, and wherein the first electrode region is the cervical region and the second electrode region is the horn region.

60. A method of ablating and/or coagulating tissue, comprising the steps of:

(a) providing an electrode carrying member, said member formed of fabric metallized with a conductive material and having non-conductive regions formed thereon to create a bipolar array of electrodes;

(b) positioning the electrodes in contact with tissue to be ablated;

(c) delivering bipolar energy to the array of electrodes, causing current to pass from the electrodes to the tissue to cause the tissue to ablate and/or coagulate; and (d) during ablation and/or coagulation of the tissue, applying suction through the electrode carrying member to cause moisture generated during the ablation and/or coagulation to pass into the electrode carrying member and away from the tissue, said suction substantially preventing formation of a low-impedance liquid layer around the electrodes.

61. The method of claim 60 further including the steps of:

(e) monitoring the impedance of the tissue undergoing ablation; and (f) terminating the ablation procedure once the impedance has reached a predetermined level.

62. The method of claim 60 wherein the electrode carrying member is shaped to approximate the shape of a uterus, and wherein step (b) includes the step of inserting the electrode carrying member into a uterus.

63. A method of ablating and/or coagulating tissue, comprising the steps of:

(a) providing an electrode carrying member comprising a moisture permeable envolope having a hollow interior, said envelope formed of fabric metallized with a conductive material and having non-conductive regions formed thereon to create an array of electrodes;

(b) positioning the electrodes in contact with tissue to be ablated;

(c) passing current through the electrodes to the tissue to cause the tissue to ablate and/or coagulate; and (d) during ablation and/or coagulation of the tissue, applying suction through the electrode carrying member to cause moisture generated during the ablation and/or coagulation to pass into the hollow interior of the electrode carrying member and away from the electrodes, said suction substantially preventing formation of a low-impedance liquid layer around the electrodes.

64. The methosd of claim 63 wherein the providing step further provides an elongate tube having a open distal end disposed within the hollow interior of the electrode carrying member, and wherein step (d) further includes applying suction to the elongate tube to draw moisture from the hollow interior of the electrode carrying member into the elongate tube.

65. The method of claim 64 wherein the providing step further provides the elongate tube to include perforations therethrough, and wherein step (d) further includes applying suction to the elongate tube to draw moisture from the hollow interior of the electrode carrying member through the performations into the elongate tube.

66. The method of claim 63 wherein the electrode carrying member is shaped to approximate the shape of a uterus, and wherein step (b) includes the step of inserting the electrode carrying member into a uterus.

67. The apparatus of claim 27 wherein the array is a bipolar array.

68. The method of claim 63 wherein the array is a bipolar array.

69. A method of ablating and/or coagulating tissue, comprising the steps of:

(a) providing an electrode carrying member having a first electrode region and a second electrode region, and electrodes having a known electrode width formed on the electrode carrying member in the first and second electrode regions, the electrodes in the first electrode region having a first electrode spacing selected to carry out ablation/coagulation to a first depth, the electrodes in the second electrode region having a second electrode spacing different than the first electrode spacing, the second electrode spacing selected to carry out ablation/coagulation to a second depth that is different from the first depth;

(b) positioning the electrodes in contact with tissue to be treated, such that the first electrode region is positioned in contact with a first tissue area and the second electrode region is positioned in contact with a second tissue area;

(c) passing current through the electrodes to the tissue to cause the tissue in the first tissue area to ablate/coagulate to approximately the first depth and to cause the tissue in the second tissue area to ablate and/or coagulate to approximately the second depth; and (d) during ablation/coagulation of the tissue, applying suction through the electrode carrying member to cause moisture generated during the ablation/coagulation to pass into the electrode carrying member and away from the tissue.

70. The method of claim 69 wherein step (b) includes the step of positioning the electrode carrying member within a uterus having a horn region, a main body region, and a cervical region, and wherein the first tissue area is the horn region and the second tissue area is the main body region.

71. The method of claim 69 wherein step (b) includes the step of positioning the electrode carrying member within a uterus having a horn region, a main body region, and a cervical region, and wherein the first tissue area is the cervical region and the second tissue area is the main body region.

72. The method of claim 69 wherein step (b) includes the step of positioning the electrode carrying member within a uterus having a horn region, a main body region, and a cervical region, and wherein the first tissue area is the cervical region and the second tissue area is the horn region.

73. A method of ablating and/or coagulating tissue, comprising the steps of:

(a) providing an electrode carrying member with an array of bipolar electrodes thereon, the electrode carrying member shaped to approximate the shape of a uterus;

(b) inserting the electrode carrying member into a uterus and positioning the electrodes in contact with tissue to be ablated;

(c) passing current through the electrodes to the tissue to cause the tissue to ablate and/or coagulate; and (d) during ablation and/or coagulation of the tissue, applying suction through the electrode carrying member to cause moisture generated during the ablation and/or coagulation to pass into the electrode carrying member and away from the tissue, wherein substantially the entire array of bipolar electrodes maintains continuous contact with the tissue to be ablated during said ablation and/or coagulation of the tissue.

74. A method of ablating and/or coagulating tissue, comprising the steps of:

(a) providing an electrode carrying member formed of a fabric metallized with a conductive metal, said metallized fabric having non-conductive regions formed thereon to create a bi-polar array of electrodes;

(b) positioning the electrodes in contact with tissue to be ablated;

(c) passing current through the electrodes to the tissue to cause the tissue to ablate and/or coagulate; and (d) permitting moisture generated during the ablation and/or coagulation to pass into the electrode carrying member and away from the tissue;

(e) applying suction through the electrode carrying means to draw the tissue into contract with the electrode carrying means and the electrodes and to facilitate moisture removal, substantially eliminates liquid surrounding the electrodes during ablation/coagulation.

75. A method of ablating and/or coagulating tissue, comprising the steps of:

(a) providing an electrode carrying member, said member formed of fabric metallized with a conductive material and having non-conductive regions formed thereon to create a bi-polar array of electrodes;

(b) positioning the electrodes in contact with tissue to be ablated;

(c) delivering bi-polar energy to the array of electrodes, causing current to pass from the electrodes to the tissue to cause the tissue to ablate and/or coagulate; and (d) during ablation and/or coagulation of the tissue, applying suction through the electrode carrying member to cause moisture generated during the ablation and/or coagulation to pass into the electrode carrying member and away from the tissue wherein the suction substantially eliminates liquid surrounding the electrodes during ablation/coagulation.

76. A method of ablating and/or coagulating tissue, comprising the steps of:

(a) providing an electrode carrying member comprising a moisture permeable envelope having a hollow interior, said envelope formed of fabric metallized with a conductive material and having non-conductive regions formed thereon to create an array of electrodes;

(b) positioning the electrodes in contact with tissue to be ablated;

(c) passing current through the electrodes to the tissue to cause the tissue to ablate and/or coagulate; and (d) during ablation and/or coagulation of the tissue, applying suction through the electrode carrying member to cause moisture generated during the ablation and/or coagulation to pass into the hollow interior of the electrode carrying member and away from the electrodes wherein the suction substantially eliminates liquid surrounding the electrodes during ablation/coagulation.

77. A method of coagulating/ablating a body cavity, comprising the steps of:

(a) providing a moisture permeable electrode member comprising an array of electrodes;

(b) inserting the moisture permeable electrode member into a body cavity and into contact with body tissue within the cavity;

(c) delivering RF energy to the electrodes to ablate the body tissue; and (d) during step (c), applying a vacuum through the moisture permeable electrode member to substantially eliminate liquid surrounding the electrodes.

78. The method of claim 77 wherein the array of electrodes is a bipolar array.

79. The method of claim 77 wherein the moisture permeable electrode member is formed of a metallized fabric having non-conductive regions separating the fabric into the array of electrodes.

80. The method of claim 79 wherein the array of electrodes is a bipolar array.

81. The method of claim 77 wherein the moisture permeable electrode member is shaped to approximate the shape of a uterus, and wherein step (b) includes the step of inserting the moisture permeable electrode member into a uterus.

82. The method of claim 77 wherein the vacuum applied in step (d) further draws the tissue into contact with the electrodes.

83. A method of coagulating/ablating tissue in a hollow body cavity, comprising the steps of:

(a) providing a moisture permeable electrode member comprising an array of electrodes;

(b) inserting the moisture permeable electrode member into a body cavity and into contact with body tissue within the cavity;

(c) delivering RF energy to the electrodes to ablate the body tissue, causing the body tissue to release liquid; and (d) applying a vacuum through the moisture permeable electrode member, causing the body cavity to collapse onto the moisture permeable electrode member and to remove the liquid from the body, the vacuum substantially preventing formation of a low-impedance liquid layer around the electrodes.

84. The method of claim 83 wherein step (d) further causes moisture liberated by the tissue during ablation to pass through the moisture permeable electrode member and away from the tissue.

85. The method of claim 84 wherein the moisture permeable electrode member includes an elongate tube, wherein the vacuum is applied through the tube, and wherein step (d) further causes the moisture to pass through the tube and out of the body cavity.

86. The method of claim 85 wherein step (d) further causes liquid present in the body cavity prior to step (c) to pass through the moisture permeable electrode member and into the tube.

87. The method of claim 85 wherein step (d) further causes the moisture to pass out of the body.

88. The method of claim 83 wherein the hollow body cavity is a uterus.

89. The method of claim 83 wherein the hollow body cavity is a gallbladder.

90. The method of claim 83 wherein the array is a bipolar array.

91. The method of claim 83 wherein step (d) is performed during at least a portion of step (c).

92. A method of coagulating/ablating tissue in a hollow body cavity, comprising the steps of:

(a) providing a moisture permeable electrode member comprising an array of electrodes and an elongate tube;

(b) inserting the moisture permeable electrode member into a body cavity and into contact with body tissue within the cavity;

(c) delivering RF energy to the electrodes to ablate the body tissue, causing the body tissue to release steam; and (d) applying a vacuum through the tube and the moisture permeable electrode member, the vacuum drawing the steam through the moisture permeable electrode, through the tube and out of the body cavity, the vacuum preventing the steam from forming a build-up of liquid surrounding the electrodes and substantially preventing formation of a low-impedance liquid layer around the electrodes.

93. The method of claim 92 wherein the hollow body cavity is a uterus.

94. The method of claim 92 wherein the hollow body cavity is a gallbladder.

95. The method of claim 92, further including the step of applying a vacuum through the tube and the moisture permeable electrode member prior to step (c), causing liquid present in the body cavity prior to step (c) to pass through the moisture permeable electrode member, through the tube and out of the body.

96. The method of claim 92, wherein step (d) further causes liquid present in the body cavity prior to step (c) to pass through the moisture permeable electrode member and into the tube.

97. The method of claim 92, wherein step (d) further causes the steam to pass out of the body.

98. The method of claim 92 wherein the array is a bipolar array.

99. The method of claim 92 wherein a portion of step (d) is performed during at least a portion of step (c).

100. A method of coagulating/ablating tissue in a hollow body cavity, comprising the steps of:

(a) providing a moisture permeable electrode member comprising a bipolar array of electrodes;

(b) inserting the moisture permeable member into a body cavity and into contact with body tissue within the cavity;

(c) delivering RF energy to the electrodes to cause the body tissue to release moisture and dehydrate, said dehydration causing the impedance of the body tissue to rise; and (d) applying a vacuum through the moisture permeable electrode member to draw the released moisture away from the tissue and through the moisture permeable electrode, said moisture removal substantially preventing the said released moisture from creating a conductive pathway between the electrodes, which facilitates allowing a rise of impedance at the electrodes that corresponds to the rise of impedance of the tissue, thereby causing flow of energy through the electrodes to terminate once dehydration of the tissue has approximately reached a desired ablation depth.

101. The method of claim 100 wherein the electrode array includes an electrode density that will cause the termination of step (d) to occur at approximately a predetermined ablation depth.

102. The method of claim 100 wherein the vacuum applied in step (d) further draws the moisture out of the body.

103. The method of claim 100 wherein the array is a bipolar array.

* * * * *